United States Patent [19]

Fernandez-Pol

[11] Patent Number: 5,668,016
[45] Date of Patent: Sep. 16, 1997

[54] METHOD OF PREPARING AND ACTIVATING SAMPLES FOR RADIOIMMUNOASSAY AND OTHER TEST

[76] Inventor: Jose Alberto Fernandez-Pol, 437 Hunters Hill Dr., Chesterfield, Mo. 63017

[21] Appl. No.: 581,072

[22] Filed: Dec. 29, 1995

[51] Int. Cl.$^6$ .................................................. G01N 1/10
[52] U.S. Cl. .......................... 436/179; 436/177; 436/180; 422/68.1; 422/72; 422/71
[58] Field of Search ............................... 436/179, 180, 436/177; 422/68.1, 72, 71, 100, 101

[56] References Cited

U.S. PATENT DOCUMENTS

| | | | |
|---|---|---|---|
| 4,999,304 | 3/1991 | Robertson | 436/45 |
| 5,243,041 | 9/1993 | Fernandez-Pol | 536/23.5 |
| 5,367,063 | 11/1994 | Bomalaski et al. | 536/23.1 |
| 5,395,753 | 3/1995 | Prakash | 435/7.1 |
| 5,494,803 | 2/1996 | Carbonell et al. | 435/7.92 |
| 5,530,100 | 6/1996 | Darling et al. | 530/383 |

OTHER PUBLICATIONS

Jose A. Fernandez-Pol et al.; Journal of Tumor Marker Oncology; Jun. 1995; Abstract 49.

*Primary Examiner*—Harold Pyon
*Attorney, Agent, or Firm*—Polster, Lieder, Woodruff & Lucchesi, LC

[57] ABSTRACT

A method of activating target proteins in a biologic sample for radioimmunoassay or other immunoassay by adding the sample to a diluent containing no calcium or magnesium, heating the mixture in a boiling water bath for a designated period of time, cooling the sample, centrifuging the mixture to isolate the activated protein containing supernatant, and then vortexing the supernatant to ensure homogeneity of the protein.

17 Claims, 9 Drawing Sheets

| TOTAL HEALTHY SUBJECTS | 147 | 64 | 18 | 17 | 0 | 0 |
|---|---|---|---|---|---|---|
| TOTAL CANCER DISEASE | 225 | <1 | <1 | 9 | 45 | 44 |
| TOTAL NONMALIGNANT DISEASE | 260 | 56 | 19 | 21 | 3 | <1 |

| TOTAL HEALTHY SUBJECTS | 147 | 64 | 18 | 17 | 0.1 | 0.1 |
|---|---|---|---|---|---|---|
| TOTAL CANCER DISEASE | 225 | 1 | 1 | 9 | 45 | 44 |
| TOTAL NONMALIGNANT DISEASE | 260 | 56 | 19 | 21 | 3 | 1 |

ASSAY FLOW CHART

| TUBE NUMBER | TUBE IDENTIFICATION | BUFFER D/Z | DILUENT P | CALIBRATORS/ CONTROLS | PRIMARY ANTIBODY | INCUBATION | 125-I PEPTIDE N | INCUBATION | 2nd Ab/PEG PRECIPITATION | INCUBATION | CENTRIFUGATION |
|---|---|---|---|---|---|---|---|---|---|---|---|
| 1,2 | TC | 0 | 0 | 0 | 0 | | 100 μL | | 0 | | |
| 3,4 | NSB | 50 μL | 150 μL | 0 | 0 | | | | 1.0 mL | | 3,000 × g FOR 20 MIN. 10 °C |
| 5,6 | MB | 50 μL | 50 μL | 0 | 100 μL | 5 MIN. ROOM TEMP | | 17 HOURS 4 °C | | 6 MIN. 4 °C | |
| 7,8 | A. 2 ng/mL | 0 | 0 | 100 μL | | VORTEX ALL TUBES | VORTEX ALL TUBES | | VORTEX ALL TUBES | | |
| 9,10 | B. 10 ng/mL | 0 | 0 | 100 μL | | | | | | | |
| 11,12 | C. 50 ng/mL | 0 | 0 | 100 μL | | | | | | | |
| 13,14 | D. 200 ng/mL | 0 | 0 | 100 μL | | | | | | | |
| 15,16 | E. 500 ng/mL | 0 | 0 | 100 μL | | | | | | | |
| 17,18 | R-MPS-1 | 50 μL | 0 | 50 μL ✻ | | | | | | | |
| 19,20 | LOW SERUM, CO | | | ✻ | | | | | | | |
| 21,22 | HIGH SERUM, CO | | | ✻ | | | | | | | |
| 23,24 | PATIENT 1 | | | ✻ | | | | | | | |
| 25,26 | PATIENT 2 | | | ✻ | | | | | | | |
| 27,28 | PATIENT n | | | ✻ | | | | | | | |

TC: TOTAL COUNTS; NSB: NON-SPECIFIC BINDING; MB: MAXIMUM BINDING; 2ndAb/PEG: SECONDARY ANTI-RABBIT ANTIBODY/PEG SOLUTION
✻ USE 50 μL OF ACTIVATED SUPERNATANT
CO: CONTROL PATIENT SERUM

METHOD OF PREPARING AND ACTIVATING SAMPLES FOR RADIOIMMUNOASSAY AND OTHER TEST

BACKGROUND OF THE INVENTION

This application is related to the co-pending application entitled METHOD OF PERFORMING RADIOIMMUNOASSAY AND KIT, Ser. No. 08/581,250, filed, and owned by the same inventor.

This invention relates generally to medical diagnostics and, more particularly to a simplified method of preparing and activating protein materials in a biologic sample, for example human serum, for radioimmunoassay or other diagnostic tests.

The test of the present invention is based on the discovery of a novel gene, denoted METALLOPANSTIMULIN (MPS), which encodes a protein associated with many human cancers. The novel DNA sequence which encodes the METALLOPANSTIMULIN is described in detail in U.S. Pat. No. 5,243,041, which is hereby incorporated by reference. METALLOPANSTIMULIN is "zinc finger" protein of subunit molecular weight approximately 10,000-Dalton is designated as "METALLOPANSTIMULIN" (MPS) since:

1) it forms a complex with metal ions such as zinc (Greek: metallo);
2) it has been detected in many different cell types (Greek: pan=all);
3) it is associated with ribosomes; and
4) it is associated with rapid cell proliferation (Latin: stimulin).

MPS is a multifunctional protein with at least three main functions:

1) it has a nuclear localization signal and it can bind specific DNA sequences probably acting as a modulator of transcription;
2) the MPS protein stimulates cell growth; and
3) the MPS protein is secreted from the cells into extracellular fluids.

Numerous experiments with human tissue culture cells and human pathological tissue specimens demonstrated that the MPS-1 mRNA and its encoded protein are expressed in normal cells to a much lesser degree than in premalignant or malignant tumor cells, and they are present at very low levels in senescent cells compared to young healthy cells.

It is believed that cancer detected early is more susceptible to therapy than cancer detected late.

Early detection of cancer is important in two general situations:

1) detection of primary disease in asymptomatic, previously undiagnosed individuals; and
2) detection of cancer recurrence in previously diagnosed and treated patients.

The ability to identify cancer at an early stage may be useful to administer an effective therapy.

A reliable test for detecting malignant cell proliferation, when the tumor is confined and effective treatment can be provided, would be of great value for the physician. At present, the majority of cancers have advanced beyond the organ of origin at the time of diagnosis.

The measurement of MPS-N and MPS-N-like materials in human serum is of primary interest in the detection of active malignant proliferative processes. For example, the results of clinical correlation studies to date indicate that MPS-N is frequently (>90% of the cases) elevated (>10 ng/mL) in a large number of active common malignancies, such as prostate, colorectal, lung and other cancers. Thus, MPS-N testing has significant value in detecting undiagnosed malignant cell proliferation and/or active oncogenic processes. The monitoring of patients with diagnosed malignancies in which changes in concentrations of MPS-N are observed is also of significant clinical value.

Figure 1A:
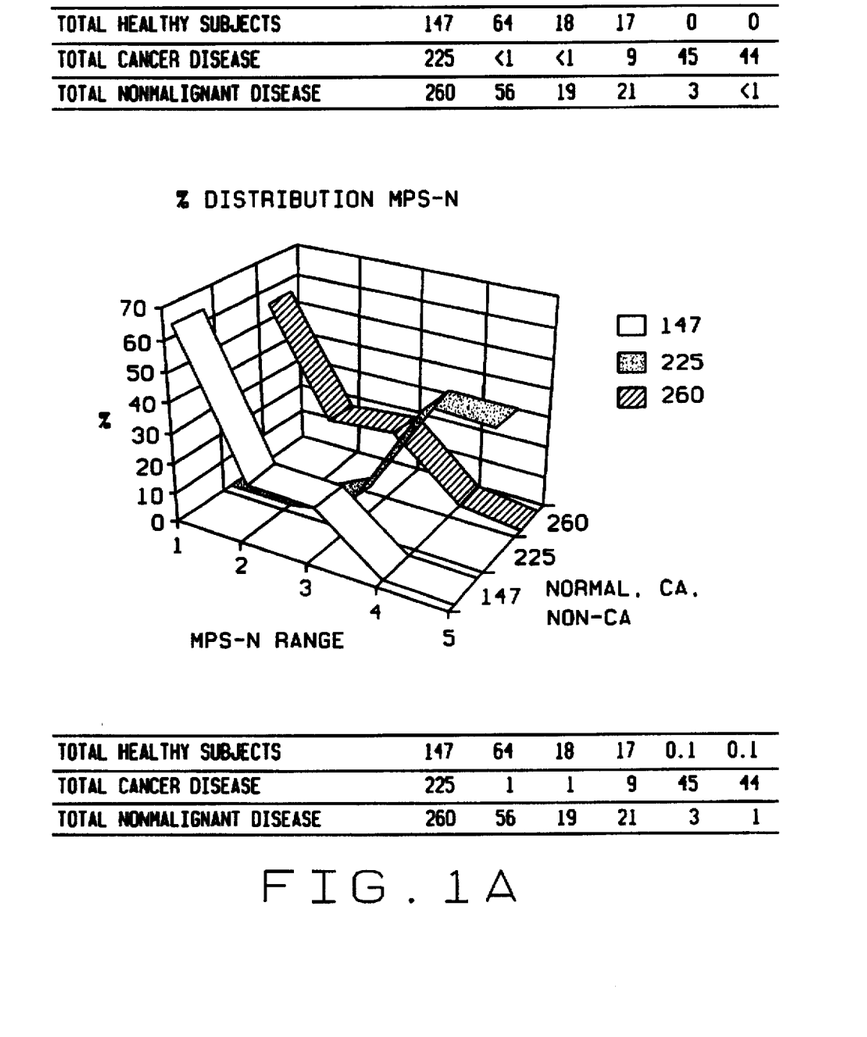
FIG. 1A is a graph illustrating the percentage distribution of MPS-N.
Figure 1B:
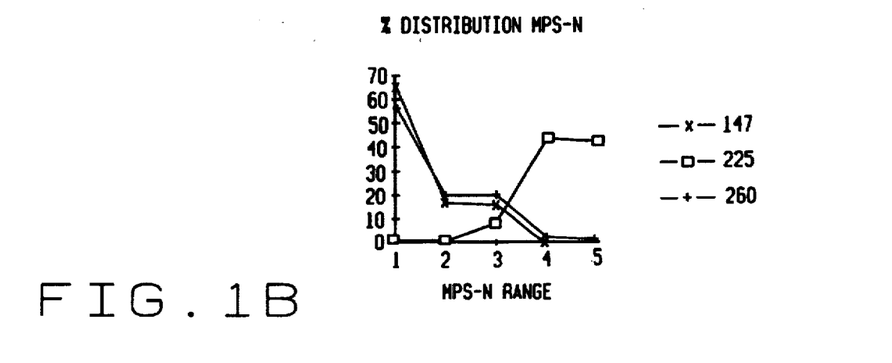
FIG. 1B is another graph illustrating the percentage distribution of MPS-N.

An extensive clinical study including 632 individuals separated in healthy subjects, active cancerous diseases, non-malignant diseases, and premalignant diseases has provided important information about the use of MPS-N in the detection of various types of cancer. The data from the clinical study is provided below in Table 1 and also illustrated graphically in FIGS. 1A and 1B.

In general, the MPS-N test was found to be useful in:

1) Detection of primary disease in previously undiagnosed individuals; and
2) Detection of cancer recurrence in previously diagnosed and treated patients.

TABLE 1

DISTRIBUTION OF MPS VALUES
NUMBER OF PATIENTS: 632

| | | Percent (ng/mL) | | | | |
|---|---|---|---|---|---|---|
| | Number | <0.7 | 7.0–10 | 10.01–20 | 20.01–50 | >50.01 |
| HEALTHY SUBJECTS | | | | | | |
| Women (19–64 years) | 20 | 70 | 20 | 10 | 0 | 0 |
| Men (21–55 years) | 20 | 65 | 10 | 25 | 0 | 0 |
| Men (50–88 years) | 107 | 62 | 20 | 18 | 0 | 0 |
| TOTAL | 147 | 64 | 18 | 17 | 0 | 0 |
| CANCEROUS DISEASES, ACTIVE | | | | | | |
| Genitourinary Tract | | | | | | |
| Prostate | 126 | 1 | <1 | 11 | 48 | 38 |
| Bladder | 6 | 0 | 0 | 0 | 33 | 66 |
| Testicular | 1 | 0 | 0 | 0 | 0 | 100 |
| Gastrointestinal Tract | | | | | | |

TABLE 1-continued

DISTRIBUTION OF MPS VALUES
NUMBER OF PATIENTS: 632

|  | Number | Percent (ng/mL) | | | | |
|---|---|---|---|---|---|---|
|  |  | <0.7 | 7.0–10 | 10.01–20 | 20.01–50 | >50.01 |
| Esophageal | 3 | 0 | 0 | 33 | 66 | 0 |
| Pancreatic | 1 | 0 | 0 | 0 | 0 | 100 |
| Hepatoma | 2 | 0 | 0 | 0 | 50 | 50 |
| Colorectal | 27 | 0 | 0 | 7 | 44 | 48 |
| Lung Cancer |  |  |  |  |  |  |
| Epithelial malignancies Head and Neck Region | 27 | 0 | 0 | 11 | 26 | 63 |
| Epithelial malignancies Central Nervous System | 6 | 0 | 0 | 0 | 66 | 33 |
| Primary Neoplasms | 1 | 0 | 0 | 0 | 0 | 100 |
| Neuroendocrine origin | 6 | 0 | 0 | 17 | 17 | 66 |
| Leukemia and lymphoma | 7 | 0 | 0 | 0 | 43 | 57 |
| Other Malignancies* | 12 | 0 | 0 | 0 | 58 | 42 |
| TOTAL | 225 | <1 | <1 | 9 | 45 | 44 |
| NONMALIGNANT DISEASES |  |  |  |  |  |  |
| Benign Prostatic Hypertrophy | 37 | 30 | 16 | 38 | 13 | 3 |
| Hepatitis, B,C. | 18 | 83 | 5 | 11 | 0 | 0 |
| Liver cirrhosis | 4 | 100 | 0 | 0 | 0 | 0 |
| Other | 201 | 58 | 21 | 20 | 1 | 0 |
| TOTAL | 260 | 56 | 19 | 21 | 3 | <1 |
| Premalignant disease |  |  |  |  |  |  |
| Colorectal Polyps | 4 | 0 | 0 | 0 | 75 | 25 |

*Other Malignancies: include cancer of unknown origins, squamous cell carcinomas, etc.

As illustrated, the quality criteria of the MPS-N test as a tumor marker, characterized by its diagnostic specificity (percentage of healthy individuals [82%] or benign diseases [75%] with a true negative test result); its sensitivity (percentage of true positive test results if cancer disease is present [98%]); and the cutoff value (concentration of MPS-N that differentiates healthy subjects or patients with benign disorders from those with premalignant or malignant disorders) clearly indicates that the MPS-N test has high specificity (>75%) and sensitivity (>98%) as a tumor marker.

The quantity of the MPS-N marker detectable is proportional to the extent of active malignancy as demonstrated by the following example of patients with prostatic carcinoma (PC). In patients not having PC, the MPS-N levels were lower than 10 ng/mL. In untreated patients having PC stages T1/T2, the MPS-N level range was 10–30 ng/mL; in stages T3/T4 the MPS-N level range was 30–50 ng/mL; and in stage M1b (distant metastasis to bone) the MPS-N levels were extremely high (100–500 ng/mL). In M1b patients that did not respond to therapy, the MPS-N levels remained very high (200 ng/mL). In M1b patients that went into remission after treatment, the MPS-N levels were greatly reduced. Thus, the increase in serum MPS-N correlated with the stage of the disease and response to therapy. The foregoing data originally was published in Fernandez-Pol, J. A, Klos, D. J., and Hamilton, P. D., *The Evaluation of Metallopanstimulin As A Novel Tumor Marker in Sera of Patients With Prostatic Carcinoma*, European J. of Nuclear Medicine, Supp. Vol. 21, No. 10; 94 (Abs)(1994); Fernandez-Pol, J. A., Klos, D. J., and Hamilton, P. D., *Metallopanstimulin As A Novel Tumor Marker In Sera Of Patients With Prostatic Carcinoma*, J. Tumor Marker Oncology, Supp. 1, June 1995 (Abs. No. A-49) p 54, which are hereby incorporated by reference.

Therefore, detection of primary prostate cancer in previously undiagnosed individuals can be accomplished by the serial measurement of MPS-N, provided that other types of cancers producing MPS-N materials are excluded. When employed for the management of prostate cancer patients, serial measurements of MPS-N is useful in detecting residual tumor and recurrent cancer after radical prostatectomy. Moreover, MPS-N is useful for assessing response of prostate cancer to therapy by prostatectomy, radiotherapy, and hormone therapy. Thus, serial measurements of MPS-N concentrations can be an important indicator in monitoring patients with prostate cancer and in determining the actual effectiveness of surgery and/or other treatments.

The MPS-N test also has significant importance in the detection of numerous types of undiagnosed common malignancies. As shown in Table 1, increased MPS-N levels have been detected with high frequency (>90% of the cases) in numerous types of common cancers such as prostate, colorectal, lung, neuroendocrine, leukemias, etc. Moreover, in patients having these types of cancers, MPS-N testing can have important value in monitoring metastatic or persistently active cancer, following chemotherapy, surgery, or radiotherapy. A persistent elevation in circulating MPS-N levels following treatment or increase in an otherwise lower level is indicative of recurrent or residual cancer and poor therapeutic response. A declining MPS-N value is generally indicative of a good response to treatment and a favorable prognosis.

Serum MPS-N can also be elevated in active nonmalignant tumorigenic processes and premalignant proliferative conditions such as benign prostatic hypertrophy and colorectal polyps, respectively (Table 1). Inflammatory conditions of the prostate, liver, intestine and colon are negative for MPS-N (Table 1, section on "Hepatitis, Cirrhosis, Other").

It has been shown that the MPS-1 DNA sequence and the protein can be used in diagnostic methods such as detection of malignant cells associated with several types of tumors. The development of a sensitive and specific radioimmunoassay (RIA) for MPS-N, using synthetic peptide technology, would make it possible to detect the very low concentrations of MPS-N and MPS-N-like materials in human blood and other body fluids. Thus, the MPS-N RIA provides a method for determining the presence of certain types of abnormal proliferative conditions and/or active oncogenic processes in patients as described below.

Although it was suggested in the '041 patent that radioimmunoassay techniques possibly could be employed to detect MPS levels, a simple and cost effective method for performing radioimmunoassay on a large number of individual samples, for example in a routine clinical screening, was not taught or disclosed. Furthermore, no reference known to the inventor teaches or suggests a low-cost kit containing materials that can easily and economically be used by a diagnostician to perform radioimmunoassay for MPS-N like materials.

More importantly, no prior art reference suggested or taught a method of activating the MPS-like proteins in the serum sample which would allow detection of the MPS-N antigen. Most intracellular proteins that are released into the circulation are carried by binding proteins such as albumin, prealbumin and other more specific carrier proteins. It is well known that antibodies developed against peptide sequences of a given protein will not react in a radioimmunoassay system against native protein because most of the epitope (antigenic determinant that interact with the specific antibody) is masked. Intracellular proteins such as MPS are amphipatic and are dimeric or tetrameric in their native, non-denatured form. Under these conditions, certain regions of the polypeptide, such as epitopes corresponding to the N-terminal region, are unavailable for interaction with antibodies. Thus, the detection of the protein by antibodies is practically impossible. For example, only small quantities (2–10 ng/mL) of MPS can be detected in the native state in patients with metastatic cancer. The detectable concentration most likely corresponds to the free, unbound monomeric form of MPS and MPS-like materials.

A number of methods could be used to release, denature, linearize and, therefore, unmask or activate the total MPS-N and MPS-N-like protein. For example, acidification with 1N hydrochloric acid will release the protein. However, to measure the MPS-N a subsequent step of neutralization with sodium hydroxide is required. Also, a denaturing chaotropic agent to linearize the protein is required, with further extraction, including an expensive and cumbersome dialysis procedure. Some of the agents employed in these methods will activate proteases which will, in turn, digest the protein of interest. These are sensitive steps that may lead to inaccurate results upon measurement of the protein. The method of using chemical activation with hydrochloric acid, neutalization with sodium hydroxide plus extraction with solvents in employed in the immunoassay test for measurement of Transforming Growth Factor Beta in serum. These procedures are time consuming and subject to error making it quite difficult to make a precise determination of MPS.

SUMMARY OF THE INVENTION

It is, therefore, among the principal objects of the present invention to provide a simplified method of activating target proteins in a sample.

Another object of the invention is to provide such a method that includes a novel procedure for activating metallopanstimulin or metallopanstimulin-like proteins in the serum sample which, in turn, allows the detection of an MPS-N antigen.

It is another object of the present invention to provide the materials needed to perform the method in a kit form.

It is yet another object of the present invention to provide a simplified method of performing radioimmunoassay to detect the levels of metallopanstimulin or metallopanstimulin-like materials in a biologic sample that allows cost-effective, large scale application of the method to detect carcinoma in a large scale patient population.

Still another object of the present invention is to provide such a method of activating target proteins and a method of performing radioimmunoassay and a kit for performing the method that is economically produced, appropriately packaged, easy to use, reliable and accurate, and well-suited for its intended purposes.

In accordance with the invention, in a method of performing radioimmunoassay to detect the level of target proteins, for example metallopanstimulin or metallopanstimulin-like materials in a biologic sample is provided wherein MPS-N and MPS-N-like molecules in the patient sample compete with radiolabeled peptide -N for sites on the anti-peptide-N-specific antibody directed towards a unique site on the MPS-1 molecule.

The novel method for activating the target proteins in the patient sample is performed as follows: In a sample, for example a biologic fluid such as sera, the target proteins are bound to carrier proteins. The target proteins, for example MPS-N or MPS-N-like proteins are activated or released from the carrier proteins by adding a calcium and magnesium-free buffered diluent to the sample and then heating the sample for an appropriate period of time.

DESCRIPTION OF THE PREFERRED EMBODIMENT

In general, the radioimmunoassay of the present invention can be performed with the reagents and in the manner as will be described in detail below.

The radioimmunoassay involves a total incubation time of 17 h at 4° C. A calibration curve and 20 patient samples can be prepared in less than an hour.

Broadly speaking, separation is attained by a precipitating solution consisting of a second antibody against rabbit primary antibody and a solution of PEG. The precipitation reaction is completed in a set time at 4° C. in an ice bath, which has been shown to yield reproducible results. The precipitate is solid, easily perceptible and non-specific binding is low. The PEG solution is supplied as ready to use.

Figure 2A:
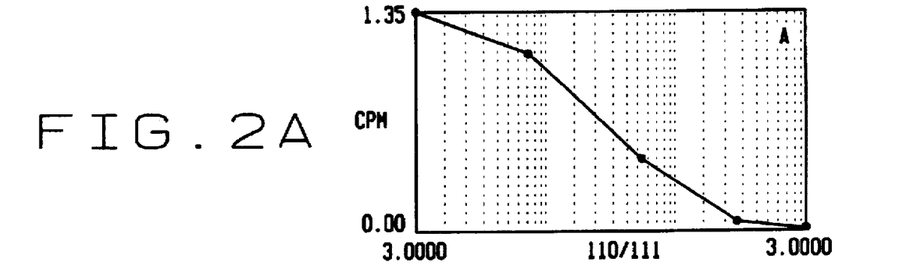
FIG. 2A is a graph illustrating the results of MPS-N test assay in semi-log point-to-point format.
Figure 2B:
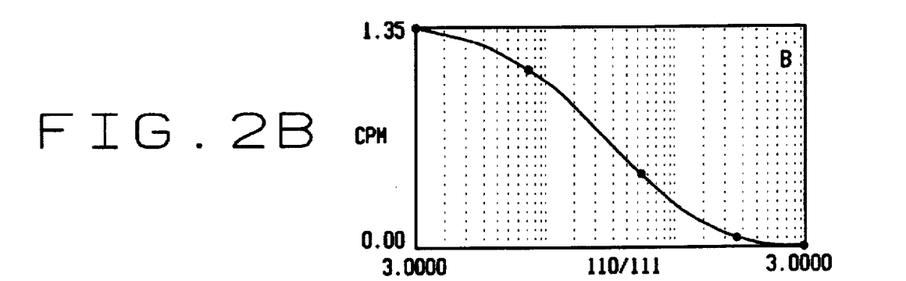
FIG. 2B is a graph illustrating the results of MPS-N test assay in 4-parameter logistic format.
Figure 2C:
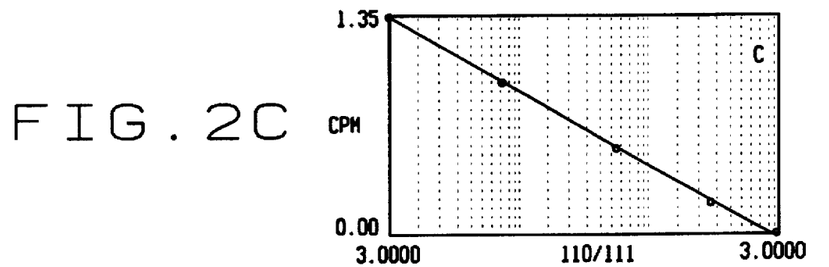
FIG. 2C is a graph illustrating the results of MPS-N test assay in Logit/Log format.

Methods for standard data analysis and quality control are provided. The assay was optimized for linearity in a Semi-Log point-to-point, 4-parameter logistic, or Logit/Log representation in the range of the calibrators (FIGS. 2A, 2B, and 2C, respectively).

The kit of the present invention includes calibrators with specific values ranging from 2 to 500 ng/mL. The calibrators are protein-based to eliminate serum protein matrix effects.

The radioactively labeled peptide-N has a high specific activity. The initial total counts are 30,000 to 40,000 cpm. The maximum binding is approximately 40–50%, which increases sensitivity and is adequate for precision.

Figure 3:
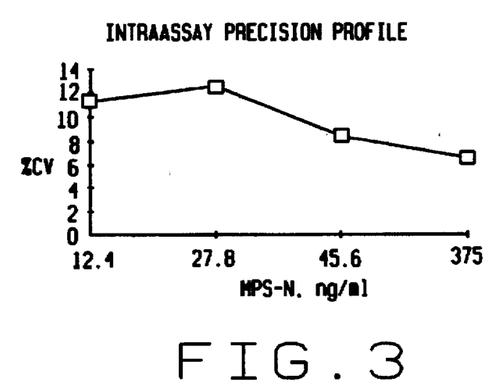
FIG. 3 is a graph illustrating intraassay precision.

Intraassay coefficient of variation is better than 13%, as shown below in Table 2 and in FIG. 3.

TABLE 2

| Intraassay Precision (Within Run) | | | | |
|---|---|---|---|---|
| Serum Sample | 1 | 2 | 3 | 4 |
| No of Replicates | 20 | 20 | 20 | 20 |
| Mean (ng/mL) | 12.4 | 27.8 | 45.6 | 375 |
| SD | 1.4 | 3.5 | 3.9 | 25.6 |
| CV (%) | 11.3 | 12.6 | 8.5 | 6.8 |

Figure 4:
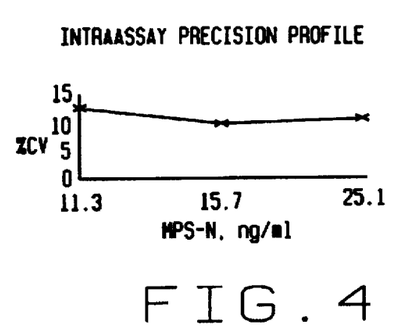
FIG. 4 is a graph illustrating interassay precision.

Interassay coefficient of variation is approximately 12%, as shown below in Table 3 and also in FIG. 4.

TABLE 3

| Interassay (Between Run) | | | |
|---|---|---|---|
| Serum Sample | 1 | 2 | 3 |
| No of Assays | 10 | 10 | 10 |
| Mean (ng/mL) | 11.3 | 15.7 | 25.1 |
| SD | 1.4 | 1.5 | 2.7 |
| CV | 12.4 | 9.6 | 10.8 |

The assay can detect as little as 2 ng/mL. No "end-of-run" assay effect has been observed in assays involving over 60 tubes, as shown in Table 5, discussed hereinafter. However, we recommend PEG precipitation in sets of 60 tubes, to minimize the effect of different incubation times with PEG.

The antiserum is highly specific for the N-terminal region of MPS. Peptide-N completely neutralizes the binding of Anti-peptide-N antibodies to human recombinant MPS-1 protein. Furthermore, a search of the sequence database Gene Bank[R] indicates that the peptide-N has less than 12% sequence homology with all the protein sequences stored in this data bank. The antibody against the N-terminal region does not react with MPS peptides corresponding to the mid-region ("Zinc Finger") or C-terminal regions of human recombinant MPS-1 protein.

Experiments have shown that the assay is accurate over a broad range of values (2–100 ng/mL). Its accuracy has been verified by recovery and dilution studies with peptide-N, human recombinant MPS-1, and human patient sera containing MPS-N. Based on a study of 147 individuals of ages from 19 to 88 years, the RIA for MPS-N has a reference range for adults of nondetectable to 10 ng/mL (82% specificity; Table 1, above).

THE KIT OF THE PRESENT INVENTION

Figure 14:
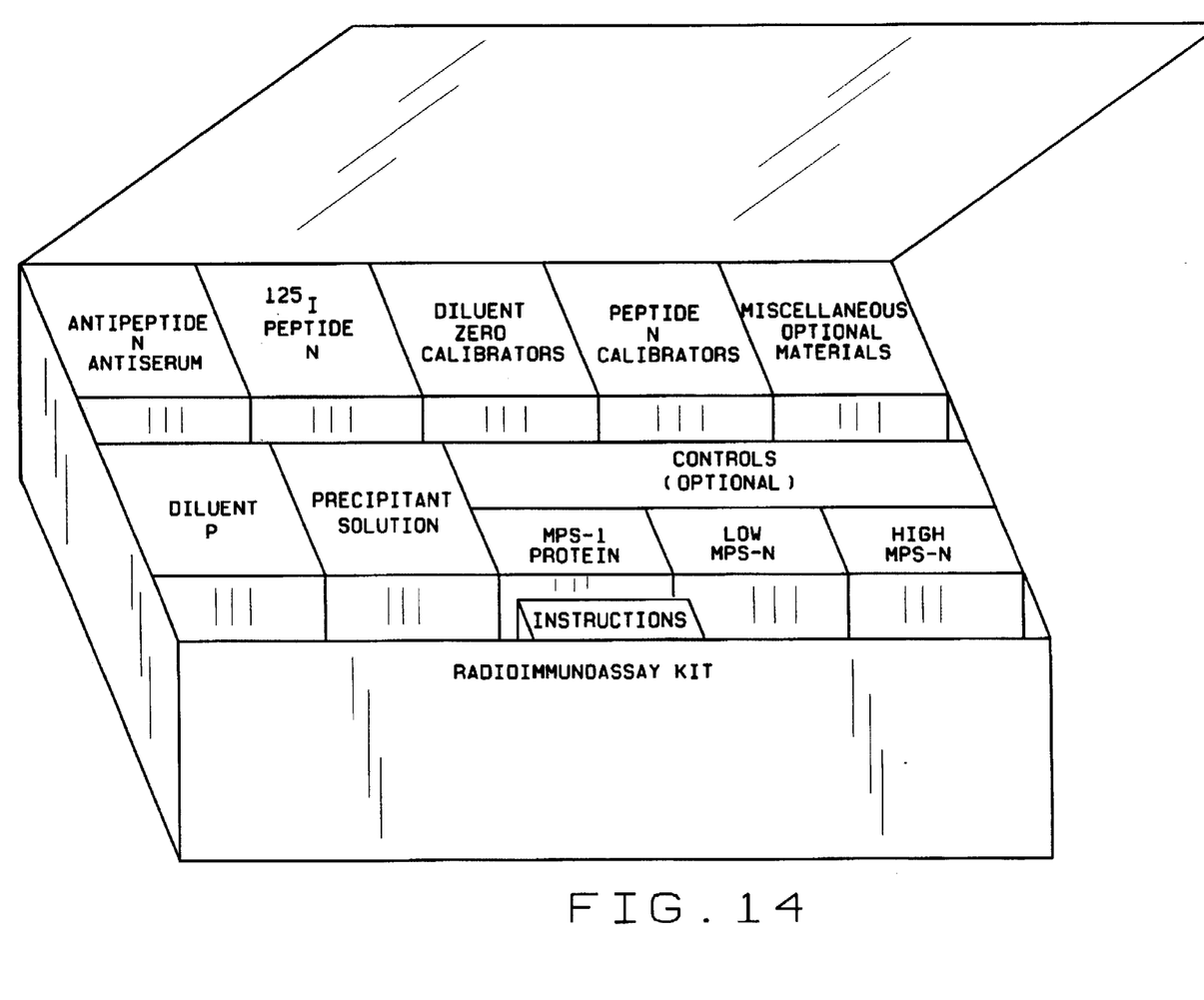
FIG. 14 is a diagram illustrating the kit for performing the radioimmunoassay of the present invention.

To perform the radioimmunoassay method of the present invention, and as will be described in detail below, the essential materials can be provided in a kit form as illustrated in FIG. 14, and comprise as follows:

One vial (7 mL) Anti-peptide N Antiserum.

The anti-peptide N antiserum contains polyclonal rabbit IgG anti-peptide N antibody, containing 0.2% $NaN_3$ (sodium azide) as a preservative. The product should be refrigerated and is stable at 2°–8° C. for at least 45 days.

One bottle (7 mL) of radiolabeled peptide N ($^{125}$I-labeled peptide-N ($^{125}$I-peptide N)).

One vial of a radiolabeled peptide N is provided. For example, in the preferred embodiment, iodinated peptide N in a protein matrix containing less than 2 uCi/vial and 0.2% sodium azide as a preservative is provided. However, any appropriate radiolabeled peptide N may be employed. Stored refrigerated the product is stable at 2°–8° C. for at least 45 days or until expiration date indicated on the label.

One bottle (10 mL) Diluent/Zero Calibrator (Buffer D/Z)

A protein matrix solution containing no detectable concentration of MPS-N (0 ng MPS-N/mL) and 0.2% sodium azide as a preservative is provided. The Buffer D/Z can be prepared as follows:

Weigh out 8 g of bovine serum albumin and 200 mg sodium axide. Dissolve in approximately 90 mL Diluent P (described in detail below). After the albumin and sodium azide are in solution, bring to 100 mL with Diluent P in a 100 mL volumetric flask. Store refrigerated, stable up to one month. Ready to use.

Peptide N calibrators (A to E).

Five bottles (1 mL each) of peptide N calibrators, identified as A,B,C,D, and E, in a protein matrix and 0.2% sodium azide as a preservative are provided. Each of these bottles, respectively, yield final concentrations in the assay robes of 2, 10, 50, 200, and 500 ng of peptide N per milliliter. The calibrators should be refrigerated and are stable at 2°–8° C. for at least 45 days.

One bottle (20 mL) Diluent P.

Diluent P is a specially prepared phosphate buffer saline solution. The Diluent P can be prepared as follows: Place 10 mL of Dulbecco's Phosphate-Buffered Saline (DPBS) 10× with no calcium and no magnesium (for example Gibco Catalog No. 14200-026) in a 200 mL volumetric flask and bring to 200 mL with deionized water. The pH should be 7.3±0.1. Filter sterilize and store at room temperature. The Diluent P can be refrigerated, stable up to 45 days.

Precipitating solution GAR/PEG (One bottle: 100 mL).

One bottle of goat anti-rabbit gamma globulin (GAR) and polyethylene glycol (PEG) in saline is provided. The precipitating solution is supplied in liquid form, ready to use.

The product should be stored refrigerated and is stable at 2°–8° C. for at least 45 days. Because a fine precipitate may form after storage at 2°–8° C., the PEG solution should be thoroughly mixed before use and used immediately after opening. The unused portion is discarded.

Occasionally one may encounter high counts in all patient samples which lead to uniformly low results. The cause is contamination or deterioration of the PEG precipitating solution. Insure that the PEG precipitating solution is used only once after opening.

STABILITY

All reagents must be brought to room temperature (18° C. to 25° C.) prior to use. After use, all reagents should be stored at 2° C. to 8° C. If precipitates or turbidity in a reagent solution is noted, this may be suspected as reagent instability or deterioration. Repeated freezing and thawing of the materials should be avoided.

CONTROLS

The control materials may be provided as optional materials in the kit or may be provided separately. MPS-N controls are prepared with human recombinant MPS-1 protein and human sera containing low and high concentrations of MPS-N protein as follows.

1. Recombinant human MPS-1 protein (One vial; lyophilized MPS-1 protein).

This control contains lyophilized baculovirus produced human recombinant MPS-1 protein at 25–50 ng/mL and 0.2% sodium azide as a preservative. The product is reconstituted with 0.5 mL distilled or deionized water and divide into aliquots and frozen at –20° C. to avoid repeated freezing and thawing when performing additional assays. The product is stable when stored at –20° C. up to one year after reconstitution.

2. Low MPS-N control (One via lyophilized human plasma).

Low MPS-N control contains approximately 2 to 7 ng of MPS-N per mL in a protein matrix and 0.2% sodium azide as a preservative. Each vial is reconstituted with 0.5 mL distilled or deionized water, divided into aliquots and frozen at –20° C. to avoid repeated freezing and thawing when performing additional assays. The low MPS-N control is stable when stored at –20° C. up to two months after reconstitution.

3. High MPS-N control (One via; lyophilized human plasma).

High MPS-N control contains approximately 30 to 50 ng of MPS-N per mL in a protein matrix and 0.2% sodium azide as a preservative. Each vial is reconstituted with 0.5 mL distilled or deionized water, divided into aliquots and frozen at –20° C. to avoid repeated freezing and thawing when performing additional assays. The control is stable when stored at –20° C. up to two months after reconstitution.

The storage conditions for the Reagents, Calibrators, and controls, is 2° to 8° C. After removal from the refrigerator, it is recommended that the materials be used immediately.

The following materials are required but not necessarily provided in the kit of the present invention:

Gamma counter

Centrifuge: refrigerated and capable of at least 14,500× g.

Test tube rack

Repeating pipettor: 2 mL (±1%)

Disposable tip precision pipettor: 50 uL (±1%)

Repeating precision pipettors: 200 uL (±1%)

Boiling water bath.

Distilled or deionized water

Volumetric pipets: 2.0, 5.0 and 10 mL.

Plain 12×75 mm polypropylene tubes, round bottom.

Micropipets: 100 uL and 10 mL. For the 100 uL additions a reliable repeating dispenser is recommended. A dispenser accurate to within 0.05 mL is recommended for the 1.0 mL addition of the PEG precipitating solution.

Vortex mixer.

Paper towels.

A bi-level(low and high) human serum-based immunoassay controls, containing MPS-N.

THE METHOD OF PERFORMING RADIOIMMUNOASSAY

PREPARATION OF REAGENTS

The reagents are prepared as follows:

Bring all reagents and specimens to room temperature (18° C.–25° C.) prior to use.

Thoroughly mix the reagents before each use by gentle agitation. Avoid cross-contamination by using a clean pipette tip for each vial and specimen. Reconstitute the lyophilized reagents with the mount specified below using distilled or deionized water. After reconstitution, allow the vials to stand at room temperature (18°–25° C.) several minutes. Mix thoroughly by gentle inversion.

SPECIMEN COLLECTION AND PREPARATION

The specimen is collected and prepared as follows:

No special patient preparation is necessary. Collect 5 mL of blood by venipuncture into plain tube (red top; marble top). Allow the blood to clot and separate the serum from the cells by centrifugation. Do not use heparinized or EDTA tubes. Avoid hemolysis. Serum is required for the RIA of MPS-N. Plasma samples should not be used. The serum specimen can be stored in a refrigerator at 2° C. to 8° C. for up to 24 h after collection. Specimens that can not be analyzed within 24 h should be frozen at –20° C. or colder. Mix thoroughly after thawing to assure consistency in the results. The procedure requires 50 uL of serum per assay tube. Unless assay immediately, samples should be aliquotted and frozen without delay after collection. Freeze and thaw only once. The samples can be stored at –20° C. for up to 3 months. Before assay, thaw the samples at room temperature and mix by inversion. Do not thaw frozen specimens by heating them in a water bath. As with numerous other assays hemolysis and lipemia may interfere with the assay. Specimens showing particulate materials, turbidity, erythrocytes, etc, should be clarified by centrifugation before testing.

PREPARATION OF THE SAMPLE FOR RIA

To circumvent the problems associated with masked epitopes on a target protein, a unique and heretofore unknown method of activating the proteins in the sample which will allow the radioimmunoassay method of the present invention, and other similar radioimmunoassay methods, to work is presented here. In this unique method, the sample, for example sera, is diluted with an appropriate buffer in a proportion that will not gel after heating, which causes the high molecular weight proteins to precipitate out, which does not activate calcium and magnesium dependent serum proteases and which allows the target protein to be linearized in a fashion that after centrifugation of the precipitated proteins, the supernatant will contain the target protein in a form that will expose all the desired epitopes.

Figure 15:
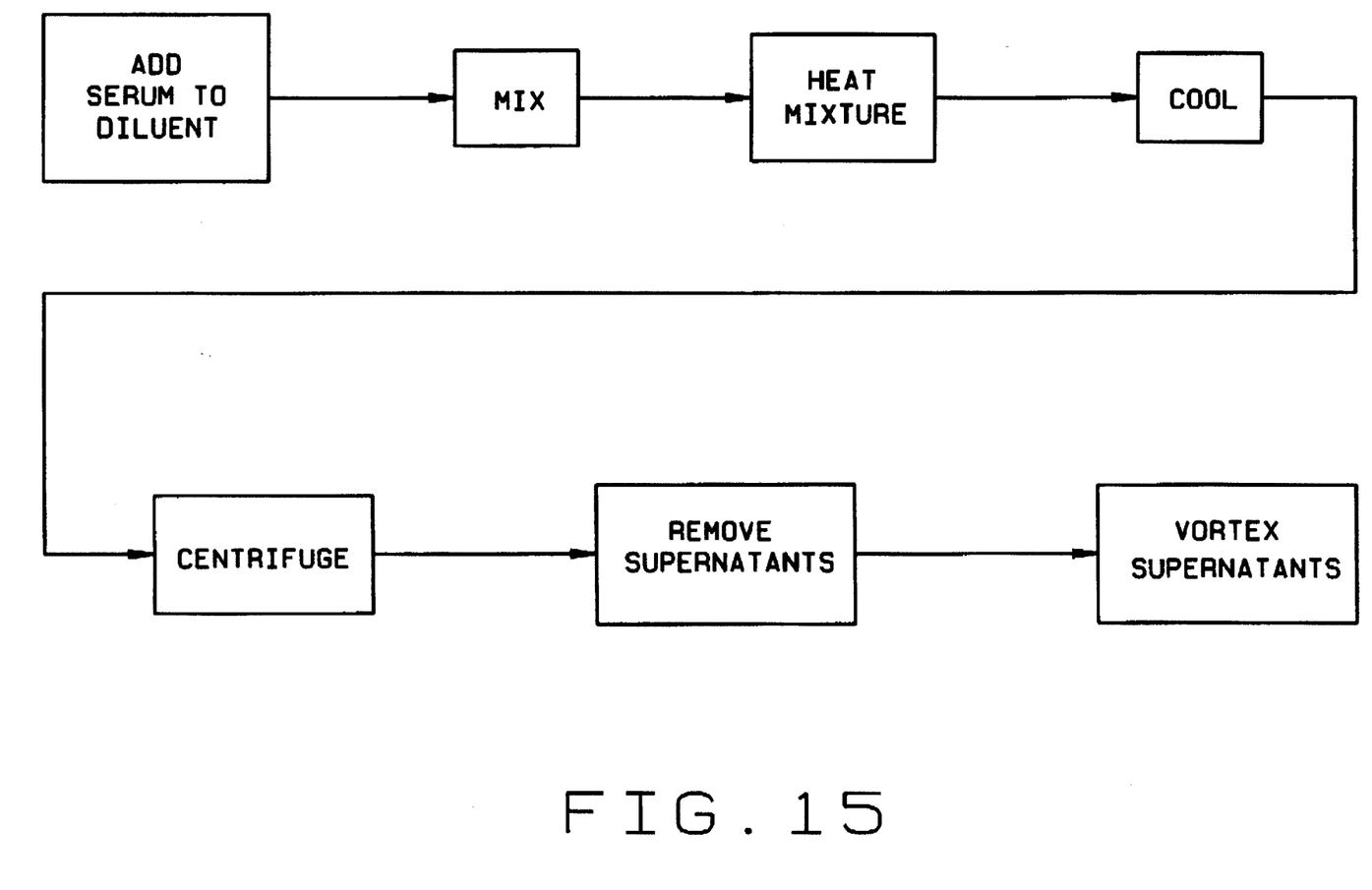
FIG. 15 is a flow chart illustrating the method of present invention for activating the target proteins.

The method of activating the target proteins is shown in FIG. 15 and described as follows:

Add about 200 μL of serum to about 400 μL of Diluent P, mix, and put in a boiling water bath for 3 to 5 minutes, preferably 3 minutes. Samples are allowed to cool at room temperature for approximately 3 minutes and then centrifuged at 14,000× g at 2°–4° C. for about 20 minutes. Supernatants are carefully removed and subsequently vortexed well to ensure homogeneity. Then, 50 μL aliquots of the supernatant are assayed in duplicate. To avoid mixing pipette close to the interface should be avoided.

This procedure also has the advantage that in samples taken from patients with cancer, many of the proteins produced by the cancer cells are heterogeneous due to the polyclonal origin of many tumors. Thus, they are mutants or are fused to other proteins. Since the fusion protein may be more sensitive to proteolysis in the region of the fusion, this method, in certain instances, generates smaller fragments of the protein (during the first minute of heating) which are susceptible to detection by immunoassay techniques.

RADIOIMMUNOASSAY PROCEDURE

Bring all kit components to room temperature and mix well before use. All Calibrators, Controls, and Patient Specimens should be tested in duplicate simultaneously. Attachment to this protocol and accuracy in all pipetting steps are fundamental to ensure excellent results. The assay procedure is as follows:

Assay for MPS-N

Figure 13:
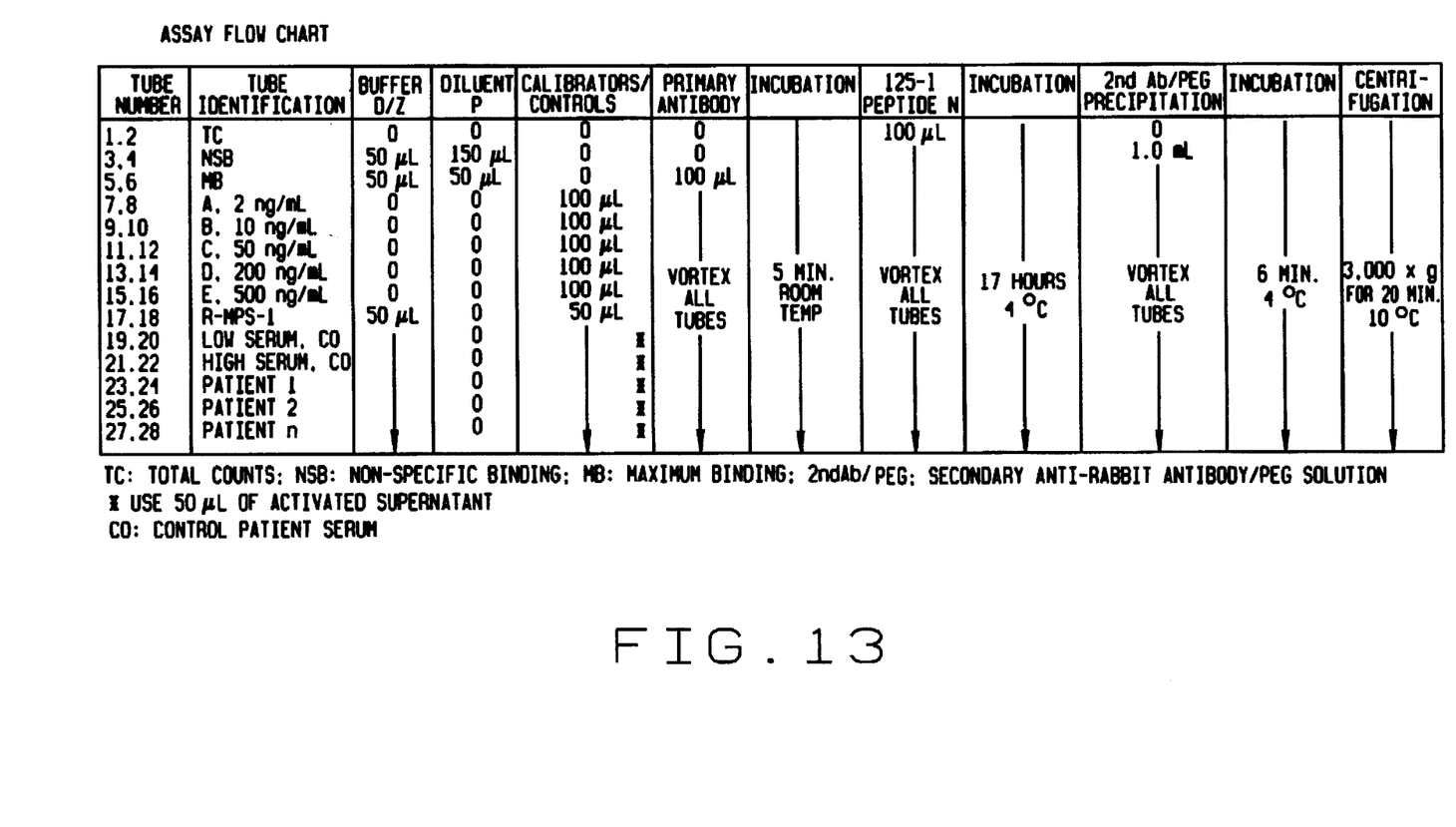
FIG. 13 is a flow chart illustrating the radioimmunoassay method of the present invention.

A preferred embodiment of an assay for MPS-N is performed according to the flow chart as illustrated in FIG. 13.

1. Label 16 tubes in duplicate to include: Total Counts (TC); nonspecific binding (NSB), Maximum Binding (MB), and calibrators A through E. Label additional tubes in duplicate for controls (R-MPS, low and high sera), and patient samples.
2. Pipette 50 uL of buffer D/Z and 150 uL of Diluent P into the NSB tubes.
3. Pipette 50 uL of buffer D/Z and 50 uL of Diluent P into the MB tubes.
4. Pipette 100 uL of calibrators (A-E) into tubes A through E.
5. Pipette 50 uL of buffer D/Z and 50 uL of controls or serum samples to the respective tubes.
6. Pipette 100 uL of Rabbit Anti-Peptide N antibodies to all tubes, except the TC and NSB tubes. Incubate 5 min at room temperature.
7. Pipette 100 uL of $^{125}$I-Peptide N into all tubes. Vortex.
8. Incubate overnight (17 h) at 4° C.
9. After overnight incubation, all samples are placed in an ice water bath.
10. Rapidly add 1.0 μL of cold, well mixed PEG precipitating solution to all tubes and vortex immediately. Allow 6 minutes for complete precipitation. Note: add PEG to sets of tubes with no more than 60 tubes per set and proceed immediately to the next step (centrifugation). Otherwise, the precipitating times are different, and this may cause in certain instances different amounts of precipitate.
10. Centrifuge 20 minutes at 3,000× g at 10° C.
11. Without delay, decant the supernatant, blot the residual droplet which remains in each tube by using an absorbent paper, retaining the precipitate for counting.
12. Count each tube for 1 minute in a gamma counter and record the counts per minute.
13. Calculate the results as described below in the description of sample data, calculation, and standard curve.

It will be appreciated that non-specific binding was measured in the absence of anti-peptide N antibodies. All results are calculated considering the dilutions made to original serum sample.

SPECIAL CONSIDERATIONS

1. When a value greater than 100 ng/mL is detected in a specimen, the specimen should be diluted with buffer D/Z and assayed again. The dilution factor should be incorporated into the calculation of results. The dilutions indicated for samples measuring greater than 100 ng/mL MPS-N are 1:1 and 1:10. The diluted sample should read within the range of the standard curve and should read greater than 2 ng/mL.

EXAMPLE

A 10-fold dilution is prepared by adding 50 uL of patient sample to 450 uL of Diluent P. The sample is mixed by vortexing. 50 uL of diluted sample is added to 50 uL of Buffer D/Z before assaying. To determine the concentration of MPS-N in the specimen, multiply the concentration of the diluted sample (read by extrapolating in the standard curve) by the dilution factor. In this case, the dilution factor is (10×3)=30.

2. Disposable pipette tips should be used. The pipette tip should be change after each sample is pipetted to prevent contamination of reagents or samples.

3. To ensure consistency in the precipitation step, the size of the assay run should be limited to 62 samples per set, which is the number that can be pipetted in 7 min.

4. A repeating pipettor should be used for addition of the PEG solution.

SAMPLE DATA, CALCULATIONS, AND STANDARD CURVE.

The data shown in FIGS. 2A–2C and Table 4, below, were obtained following the method of the present invention. They illustrate the expected results of the procedure. Because the calibrator values are lot-specific, the results shown in FIG. 2A–2C and Table 4 should not be used to calculate results from another assay. The MPS-N assay results can be calculated either manually or by using computer programs.

TABLE 4

EXAMPLE OF DATA

| Tube | Description | Duplicate CPM | Average CPM | MPS ng/mL |
|---|---|---|---|---|
| 1 | TC | 25415 | | |
| 2 | | 26213 | 25814 | |
| 3 | NSB | 91.3 | | |
| 4 | | 90 | 90.5 | |
| 5 | 0 ng/mL Calibrator | 14830 | | |
| 6 | (MB) | 14584 | 14707 | |
| 7 | 2 ng/mL Calibrator A | 14083 | | |
| 8 | | 13947 | 14015 | |
| 9 | 10 ng/mL Calibrator B | 11818 | | |
| 10 | | 11595 | 11607 | |
| 11 | 50 ng/mL Calibrator C | 6195 | | |
| 12 | | 6286 | 6241 | |
| 13 | 200 ng/mL Calibrator D | 1689 | | |
| 14 | | 1661 | 1675 | |
| 15 | 500 ng/mL Calibrator E | 785 | | |

TABLE 4-continued

EXAMPLE OF DATA

| Tube | Description | Duplicate CPM | Average CPM | MPS ng/mL |
|---|---|---|---|---|
| 16 | | 775 | 780 | |
| 17 | R-MPS | 7471 | | |
| 18 | | 7238 | 7355 | 36 |
| 19 | Low Control Serum | 13775 | | |
| 20 | | 13674 | 13725 | 2.45 × 3 = 7.4 |
| 21 | High Control Serum | 8181 | | |
| 22 | | 8477 | 8329 | 27 × 3 = 81 |
| 23 | Patient Specimen A | 3294 | | |
| 24 | | 3253 | 3274 | 123 × 3 = 369 |
| 25 | Patient Specimen B | 11679 | | |
| 26 | | 10806 | 11243 | 11.5 × 3 = 34.5 |
| 27 | Patient Specimen C | 13153 | | |
| 28 | | 13036 | 13095 | 3.8 × 3 = 11.4 |

Quality Control Parameters: TC = Total Counts; NSB: Non-specific binding MB = Maximum binding = 57.0%
% Intercepts: ED20: 136.2 ng/mL; ED50: 36.0 ng/mL; ED80: 9.60 ng/ml
Duplicate CPM column = CPM − NSB A. Manually-generated Standard Curve:

The standard curve is generated using peptide-N calibrators as follows:

1. The duplicate counts for non-specific binding (NSB) tubes are averaged.
2. The average cpm for the NSB tubes are subtracted from the cpm of maximum binding (MB), calibrators (A–E), controls, and patient sample tubes.
3. The percent maximum binding (% MB/TC) may be calculated for quality control.
4. The percent bound for each determination (B/MB X 100) is calculated by dividing the corrected average counts for each determination by the maximum binding (MB) tube×100.
5. The standard curve is generated by plotting CPM or % B/MB on the ordinate against the calibrator concentrations on the abscissa using semi-log paper.
6. The concentration of MPS-N for the unknown samples can be estimated by extrapolation.
7. Patient sample calculation: Multiply the result by the corresponding dilution factor. For example, 3X in the case of the standard dilution procedure (Table 4).

B. Computer-generated Standard Curves:

Numerous computer programs may be use to calculate the results of the MPS-N test assay. The examples shown in FIGS. 2A, 2B and 2C were generated using one of such programs (Packard Instrument Co., Meriden Conn.). FIG. 2A shows a Semi-Log Point-to-Point plot; FIG. 2B shows a Four Parament Logistic plot; and FIG. 2C shows a Logit/Log plot. After appropriate corrections, the program automatically connects the points between the mean of the calibrator duplicates. The values of the unknown samples are automatically extrapolated.

ACCEPTABILITY OF RIA RESULTS

Assay runs are acceptable if the following criteria are met:

Test should only be performed by a qualified technologist or technician who has been properly trained and is familiar with the information provided in the product insert. Values for duplicate determinations are within 13% of the mean CPM. The samples that have duplicate CPM values that differ from the mean CPM by more than 13% should be re-tested. The calibrators and control concentrations should fall within 13% of the value indicated in the vial. Laboratory temperature was between 20°–26° C. Each patient sample is run in duplicate as are all blanks, controls, and standards with no more than 20 unknowns per single run. If the result is greater than 100 ng/mL, the sample is re-run using a 1:1 and 1:10 dilution of patient serum; use buffer D/Z as the diluent. Multiply the result by dilution factor. Gamma counter must meet quality control requirements before being used to count tubes. Count all tubes in a gamma counter for one minute with the window suitably adjusted for Iodine-125.

QUALITY CONTROL

Good quality control includes the use of control samples within each assay to ensure that all protocols and reagents are performing correctly. The MPS-N assay contains all the necessary controls that can be used to validate the assay performance. The coefficient of variation for all calibrators and controls should be less than 13%. It is a worthy laboratory practice to record for each assay the dates, reconstitution of reagents, and QC parameters.

Sample handling:

Carefully follow the instructions for handling and storage of patient samples. Assay calibrators, controls, and patient samples should always be done in duplicate. It is a good practice to space duplicate control tubes throughout the assay to confirm the absence of any significant drift.

Controls:

Controls (peptide N; 5 and 25 ng/mL) or serum pools with at least two MPS-N concentration levels (high and low) should be regularly assayed as unknowns. The results should be charted daily using Levey-Jennings plots for quality control.

Centrifugation:

Centrifugation at 14,000× g for 20 min at 2°–4° C. for sample preparation and at 3,000× g for 20 min at 10° C. for PEG precipitation should be strictly followed. A high-speed, refrigerated centrifuge is required.

QC Parameters:

The inventor recommends the study of performance of the assay by using the following parameters:

TC: Total Counts (counts per minute; CPM)
% NSB (Non-Specific Binding)=100×(Average NSB Counts/Total Counts)
% MB (Maximum binding)=100×(Average MB Counts/Total Counts)
20, 50, and 80% intercepts. For example: 20%=peptide-N concentration at 20 percent bound; etc.

PERFORMANCE CHARACTERISTIC

The reliability of the MPS-N RIA procedure was evaluated by examining the reproducibility of measurements on selected samples that represent the range of values found in human sera, with particular reference to the low end of the RIA curve (10–30 ng/mL).

Intraassay Precision:

Within run precision was determined by assaying samples containing various concentrations of MPS-N. Each sample was assayed 20 times in a single assay. The data and statistics are shown in Table 2 above and illustrated by FIG. 3.

Interassay Precision:

Between run precision was determined by duplicate measurements of low and medium level patient samples in a series of 10 individual assays. The data and statistics are shown in Table 3, above and by FIG. 4.

Sensitivity:

The detection limit of the assay, or minimal detectable dose is approximately 2 ng/mL.

Specificity:

The antiserum is highly specific for the N-terminal domain of the human MPS-1 sequence. Peptide N completely neutralizes the binding of anti-peptide N antibodies to human recombinant MPS-1. With the exception of the immunoreactive MPS-N material in the human sera containing the N-terminal sequence of MPS-1 and the cellular MPS-1 proteins, the antiserum exhibits no significant cross-reactivity with other human cellular components.

Drift:

Delays in additions of reagents may result in positional(or "end of-run") effects. The results of the measurement of the same samples in various positions show that there is no significant effect in assays involving 62 tubes or less. Thus, it is recommended that the samples are handled as sets of 60 when the PEG precipitating solution is added. This approach prevents any significant variation in the time of precipitation which may potentially lead to "end-of-rim" effects. The data is shown below in Table 5.

TABLE 5

Drift (Values represent ng/mL)

| Tubes | Sample 1 | Tubes | Sample 2 |
| --- | --- | --- | --- |
| 25–26 | 31.2 | 31–32 | 376.2 |
| 33–34 | 30.3 | 35–36 | 389.7 |
| 45–46 | 30.9 | 43–44 | 363.3 |
| 53–54 | 25.5 | 51–52 | 380.7 |
| 63–64 | 30 | 61–62 | 389.3 |

Figure 7:
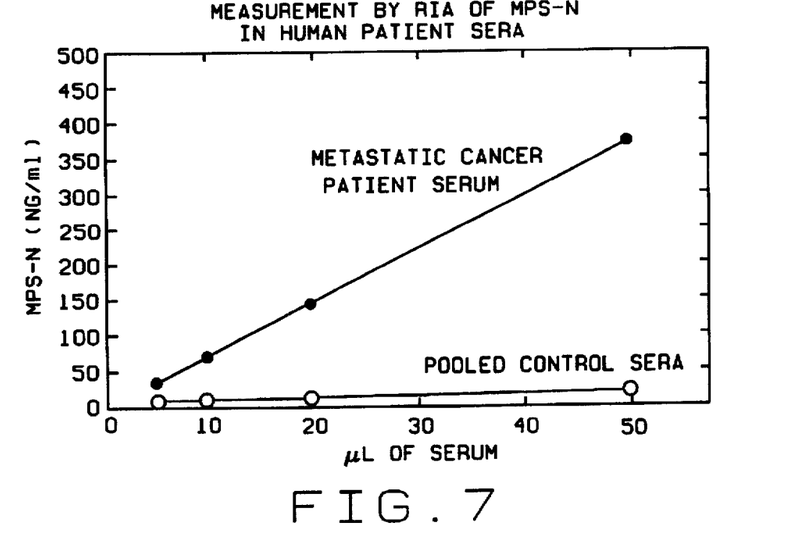
FIG. 7 is a graph illustrating the measurement of MPS-N in human sera by the radioimmunoassay method of the present invention.
Figure 8:
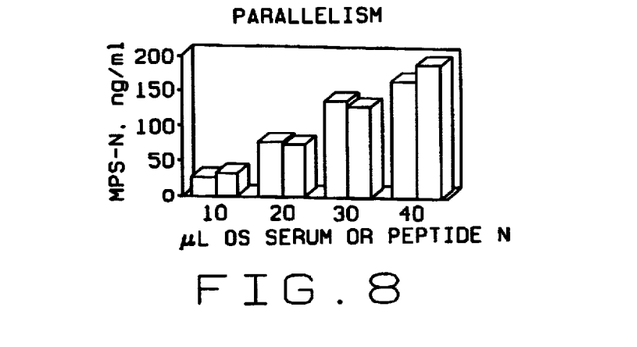
FIG. 8 is a graph illustrating parallelism.
Figure 9:
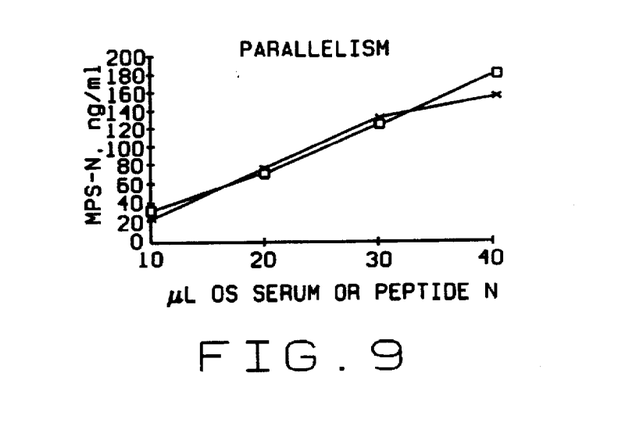
FIG. 9 is a graph illustrating parallelism.

Parallelism:

Parallelism is defined as the extent to which the dose-response relationship between two materials (i.e., calibrator versus unknown specimens) is constant for the examined range of concentrations. To document parallelism, pooled control sera and cancer patient samples were assayed both undiluted and diluted with buffer D/Z. The example shown in FIG. 7 demonstrates that the RIA procedure maintains an excellent linearity under dilution with a variation that is within the precision of the assay. In addition, the data presented in Table 6 show both parallelism and the immunological identity of human serum MPS-N and peptide N. See also FIGS. 8 and 9.

TABLE 6

PARALLELISM AND IMMUNOLOGICAL IDENTITY

| Serum, uL | Serum, ng/mL | Peptide-N, ng/mL |
| --- | --- | --- |
| 10 | 25.5 | 31.7 |
| 20 | 76 | 73 |
| 30 | 137 | 131 |
| 40 | 167 | 190 |

These results also verify the absence of a significant protein-matrix effect: The peptide N-based calibrators are well matched to the supernatant matrix of the typical normal subject and cancer patient samples.

Figure 10:
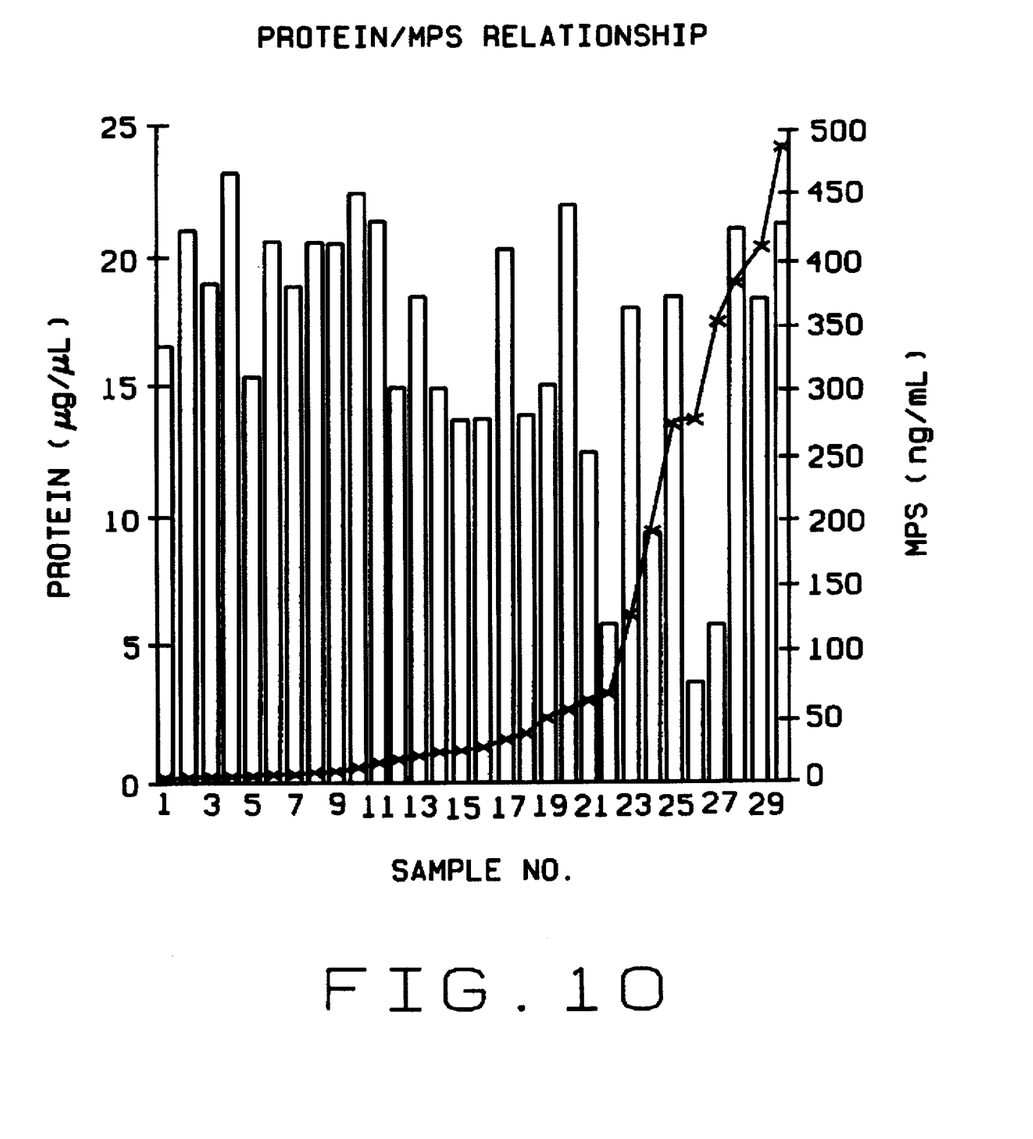
FIG. 10 is a graph illustrating the relationship between protein and MPS.

Protein Concentration:

To determine if there is any effect of protein concentration in the MPS-N determinations, experiments were performed with the supernatants of patient samples which showed large variations in supernatant protein concentrations. The protein concentrations in the supernatants were measured in duplicate in 30 separate individual patient samples. In aliquots of the same samples, the MPS-N levels were determined in duplicate. The results, shown below in Table 7 as well as in FIG. 10, show that the concentrations of MPS-N do not correlate with protein concentrations in the supernatant. The results also indicate that the assay maintains good correlation with the clinical condition even in the presence of extreme variations in protein concentration which are frequently found in cancer patients.

TABLE 7

Protein/MPS Relationship

| Sample No. | Protein ug/uL | MPS ng/mL |
| --- | --- | --- |
| 1 | 16.6 | 0.5 |
| 2 | 21 | 0.8 |
| 3 | 19 | 1 |
| 4 | 23.2 | 1.1 |
| 5 | 15.4 | 1.5 |
| 6 | 20.6 | 1.9 |
| 7 | 19 | 3.1 |
| 8 | 20.6 | 3.5 |
| 9 | 20.6 | 4.6 |
| 10 | 22.4 | 6.9 |
| 11 | 21.4 | 10.17 |
| 12 | 15 | 13.8 |
| 13 | 18.6 | 17.2 |
| 14 | 15 | 17.8 |
| 15 | 13.8 | 18.2 |
| 16 | 13.8 | 22.5 |
| 17 | 20.4 | 31.9 |
| 18 | 14 | 32.5 |
| 19 | 15.2 | 46.2 |
| 20 | 22 | 52.7 |
| 21 | 12.6 | 59.1 |
| 22 | 6 | 63.3 |
| 23 | 18.2 | 123.2 |
| 24 | 9.6 | 188.8 |
| 25 | 18.6 | 271.7 |
| 26 | 3.8 | 273.7 |
| 27 | 6 | 351.1 |
| 28 | 21.2 | 382.5 |
| 29 | 8.6 | 407.9 |
| 30 | 21.4 | 483.6 |

Recovery:

Recovery was determined by measuring the increase in analyte concentration in a sample after adding a known amount of the analyte. For this purpose, various quantities of recombinant MPS-1 (R-MPS-1) or peptide-N were added to human sera containing endogenous MPS-N and the samples were assayed in duplicate. Three spiking solutions were prepared using the zero calibrator as diluent. The solutions (A, B and C) were made to represent 20 ng/mL of R-MPS-1, or 20 and 40 ng/mL Peptide N, respectively. To calculate expected values, the measured serum value was added to the measured R-MPS-1 or measured Peptide N values. Percent recovery is equal to the observed concentration of MPS-N divided by expected concentration of MPS-N times 100. The results shown in Table 8 below, demonstrate a recovery range of 94–99%.

TABLE 8

Recovery (values represent ng/mL)

| Sera Samples | R-MPS-1 Added | Peptide-N Added | Expected Concentration | Observed Concentration | %* Recovery |
| --- | --- | --- | --- | --- | --- |
| 2.4 | 21.8 | 0 | 24.2 | 23.9 | 99 |
| 15.2 | 19.4 | 0 | 34.6 | 34 | 98 |
| 10.5 | 0 | 19.1 | 29.6 | 27.7 | 94 |
| 10.5 | 0 | 39 | 49.5 | 48.2 | 97 |

TABLE 8-continued

Recovery (values represent ng/mL)

| Sera Samples | R-MPS-1 Added | Peptide-N Added | Expected Concentration | Observed Concentration | %* Recovery |
|---|---|---|---|---|---|

*% Recovery: Observed concentration of MPS-N divided by expected concentration of MPS-N × 100.

EXPECTED VALUES

MPS-N concentrations were determined in 632 individual samples. The relative distribution of MPS-N concentrations in healthy subjects, patients with various types of active cancer and patients with non-malignant diseases is presented in Table 1, above. The distribution for cancerous diseases consisted of active cases (clinical evidence of disease progression). In this study, 82% of the healthy subjects had MPS-N concentrations of 10 ng/mL or less.
Normal levels.

Figure 11:
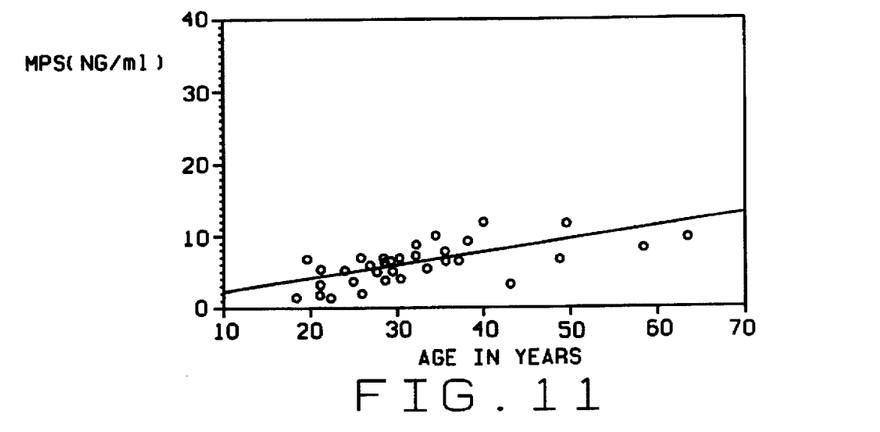
FIG. 11 is a graph illustrating adult normal MPS values as a function of patient age.
Figure 12:
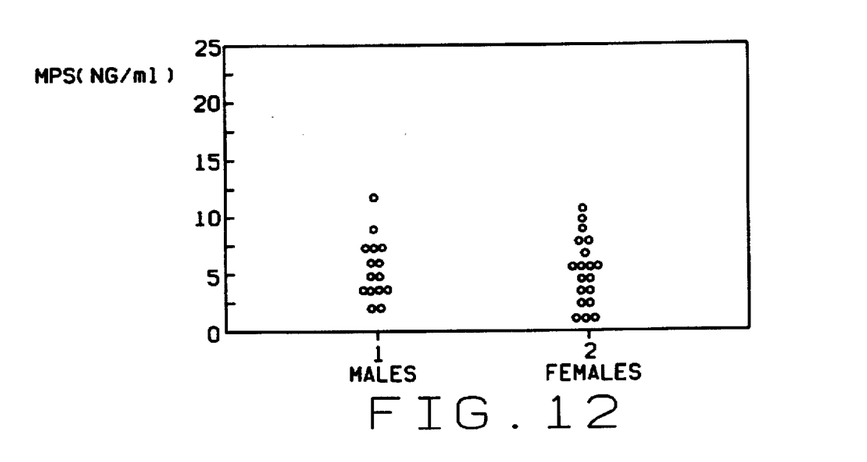
FIG. 12 illustrates the comparison of MPS values between men and women.

The results of studies with healthy subjects indicate a reference range for adults (19–88 years) of non-detectable to 10 ng/mL (82% of the healthy population). FIG. 11 shows that in healthy subjects the MPS-N levels increase significantly with age, from approximately 4 ng/mL at age 20 years to about 10 ng/mL at age 50 years. FIG. 12 shows that there is no difference in MPS-N levels between male and female healthy subjects. Laboratories using the MPS-N test should consider these results a guideline only. Because the concentration of MPS-N is age related, and the possibility that different populations may have different base lines, it is necessary that each laboratory establish the normal range for a healthy population or for the population of interest.

If the assay value of a patient sample is between 10 and 20 ng/mL (17% of the presumed healthy subjects fall in this category; Table 1), it is recommended that a new MPS-N measurement is performed in 3 months.
Example of expected values in detection of Prostate Cancer.

A retrospective clinical trial was conducted to test the effectiveness of MPS-N measurement to detect abnormal cell proliferation and/or active oncogenic processes related to prostate cancer. A total of 126 men 49 to 85 years of age were included in this study (Table 1). These studies demonstrated that the majority (97% or 122/126) of the active cancers were detected, when a cutoff value of 10 ng/mL MPS-N was used (Table 1). Further studies indicate that the levels of MPS-N correlate with the clinical stage of disease. Thus, in patients suspected of having prostate cancer, MPS-N elevations greater than 10 ng/mL may indicate the existence of an abnormal proliferative and/or active oncogenic process that requires further clinical investigation by a physician.
Example of expected values for prognosis and management of prostate cancer.

Figure 5:
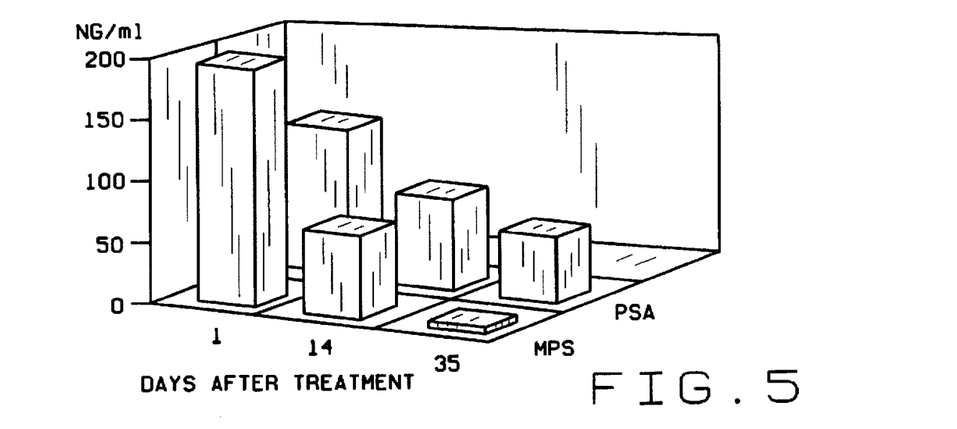
FIG. 5 is a graph illustrating post treatment decrease in serum MPS in a patient with prostate cancer.
Figure 6:
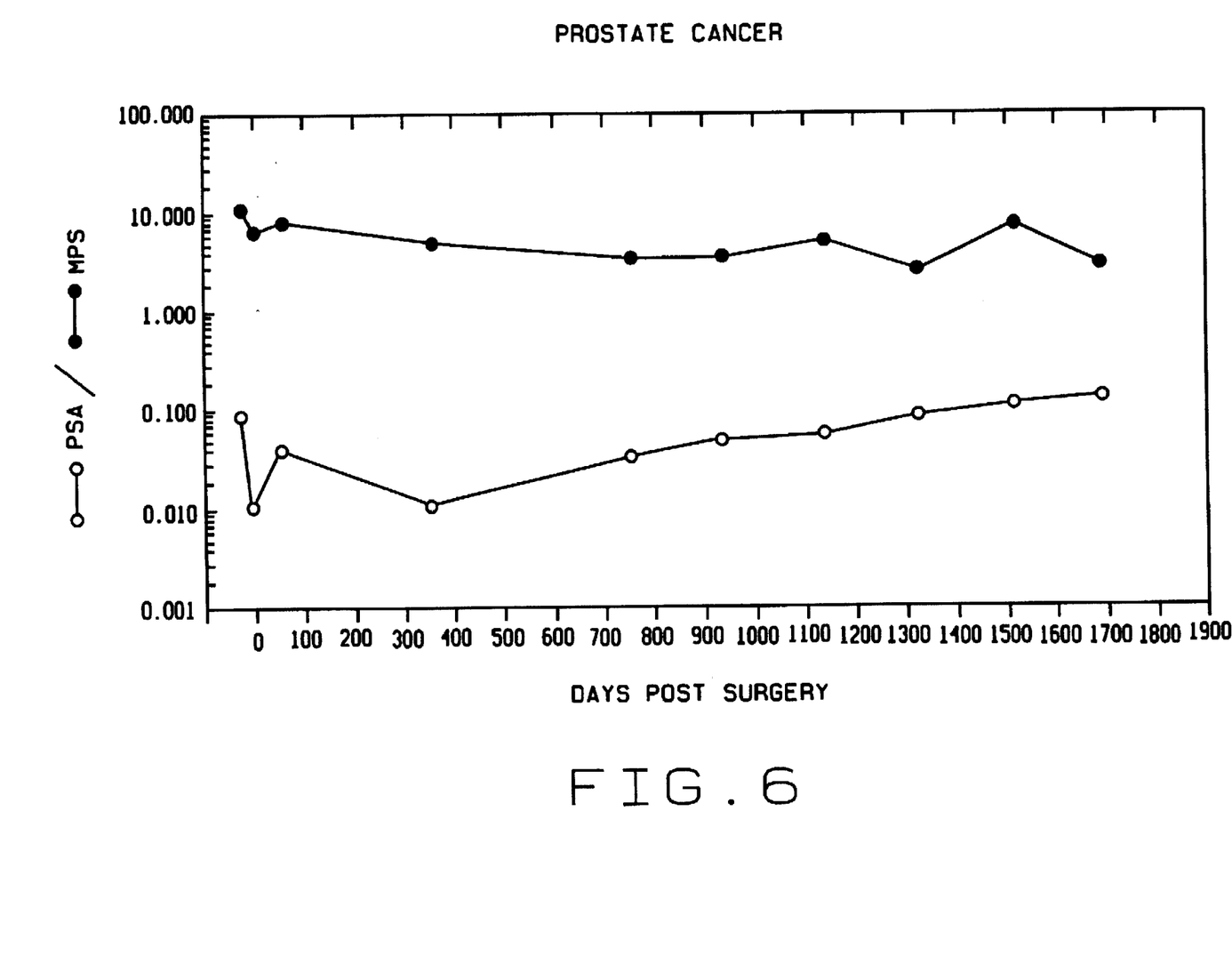
FIG. 6 is a graph comparing MPS and PSA values post-surgically in a patient with prostate cancer.

FIG. 5 illustrates the early decrease in MPS-N levels in a patient with prostate cancer which was treated with prostatectomy, chemotherapy and radiotherapy. The MPS-N levels decreased from 189 ng/mL (day 1), 73.8 ng/mL (day 14), to 8.7 ng/mL (day 35) after treatment, which correlated with clinical evidence of successful therapy. Moreover, long-term follow up studies demonstrated that three patients free from prostate cancer disease for approximately 4 years after treatment showed MPS-N levels consistently lower than 10 ng/mL in serial determinations for approximately 4 years after treatment. An example of one of such cases with a follow up of 4.6 years after treatment is shown in FIG. 6.

FALSE POSITIVE AND FALSE NEGATIVE RESULTS IN VARIOUS PATHOLOGICAL CONDITIONS

As with any other medical test that determines the concentration of proteins in the human serum, severe/extreme cases of organ failure such as liver, kidneys, massive brain damage, massive muscle damage, septicemia and in terminal patients, the test can show falsely positive or negative results. For example, renal insufficiency may impair the normal excretion mode of MPS-N and lead to false-positive results. In addition, iatrogenic influences such as colonoscopy, cystoscopy, etc, may lead to the release of MPS-N protein from the cells into the circulation. Iatrogenic medications may also cause alterations in the release of MPS-N protein into the circulation.

FALSE POSITIVE RESULTS DURING PREGNANCY

Because the MPS-N protein is produced by the embryo and it is also produced and released by the trophoblastic cells of the developing placenta, the MPS-N protein is present in the sera of pregnant women. Thus, the MPS-N test cannot be used in pregnant women.
Interfering Substances In vitro interferences can by caused by EDTA, citrate, and heparin. In vivo interferences can be caused by extremely high concentrations of hemoglobin, bilirubin or triglycerides.

It will be understood from the foregoing discussion that various changes and modifications may be made in the methods and the kit of the present invention without departing from the scope of the appended claims. For example, although the method of activating the protein is discussed with reference to activating MPS-N or MPSN-like proteins for radioimmunoassay, it will be appreciated by those skilled in the art that the method can be used to activate other target proteins for radioimmunoassy or other immunoassay procedures. Therefore, the foregoing description, tables and accompanying drawings should be viewed as illustrative only and not in a limiting sense.

I claim:

1. A method of activating a protein in a sample for diagnostic procedures comprising the steps of:

diluting a predetermined quantity of the sample with a predetermined quantity of a diluent, said diluent having no calcium and magnesium;

mixing the serum and diluent;

heating the serum and diluent to 100° C. for a predetermined time period;

cooling the serum and diluent;

centrifuging the serum and diluent;

removing a supernatant liquid; and vortexing the remaining material; wherein the predetermined period of time for heating the sample and diluent is approximately 3 to 5 minutes; wherein the diluent is a phosphate buffer saline solution without calcium and magnesium.

2. The method of claim 1 wherein the step of cooling the serum and diluent further comprises cooling at room temperature for a predetermined period of time.

3. The method of claim 1 wherein the step of centrifuging the serum and diluent further comprises centrifuging at 14,000× g at 2°–4° C. for approximately twenty minutes.

4. A method of releasing bound target proteins in a sample for radioimmunoassay testing comprising the steps of:

diluting a predetermined quantity of sample with a predetermined quantity of a phosphate-buffered saline diluent, said diluent having no calcium and magnesium, to form a in a mixture of said sample in said diluent;

heating the mixture in a boiling water bath to 100° C. for a predetermined amount of time;

centrifuging the mixture; and removing a protein-containing supernatants; wherein the predetermined period of time for heating the sample and diluent is approximately 3 to 5 minutes; wherein the diluent is a phosphate buffer saline solution without calcium and magnesium.

5. The method of claim 4 wherein the predetermined amount of sample is about 200 µL.

6. The method of claim 4 wherein the predetermined amount of diluent is about 400 µL.

7. The method of claim 4 wherein the mixture is heated for approximately three minutes.

8. The method of claim 4 further comprising a last step of vortexing the supernatants to ensure homogeneity of the activated proteins.

9. The method of claim 8 further comprising a last step of preparing individual aliquots of the supernatant for assaying.

10. A method of activating and releasing target proteins in a biologic fluid for radioimmunoassay comprising the steps of:

adding about 200 µL of biologic fluid to about 400 µL of buffered saline solution to form a biologic fluid in buffered saline solution mixture;

heating said mixture boiling water bath to 100° C. for approximately three minutes;

cooling the mixture at room temperature;

centrifuging the mixture at approximately 14,000× g at about 2 to 4 degrees C. for approximately twenty minutes;

removing the activated protein containing supernatants from the centrifuged mixture; and vortexing the supernatants to ensure homogeneity of the activated proteins; wherein the diluent is a phosphate buffer saline solution without calcium and magnesium.

11. The method of claim 10 further containing the step of dividing the vortexed supernatants into individual aliquots.

12. The method of claim 11 wherein the individual aliquots are about 50 µL.

13. A method of activating by unbinding target proteins in a biologic fluid sample from non-target proteins for analysis of the target proteins comprising the steps of:

adding a predetermined amount of serum containing the target proteins bound to non-target proteins to a physiologically buffered saline solution, said buffered saline solution having no magnesium and calcium; and heating the serum and diluent at approximately 3 to five minutes so as to activate the target proteins by unbinding the target proteins from non-target proteins; wherein the diluent is a phosphate buffer saline solution without calcium and magnesium.

14. The method of claim 13 wherein step of heating the serum and diluent further comprises heating the serum and diluent in a boiling water bath.

15. The method of claim 13 further comprising the step of centrifuging the serum and diluent after the step of heating.

16. The method of claim 15 further comprising the step of removing the supernatant after the step of centrifuging.

17. The method of claim 16 further comprising the step of vortexing the supernatants after the step of removing the supernatants.

* * * * *